United States Patent [19]
Cohen

[11] Patent Number: 5,897,864
[45] Date of Patent: Apr. 27, 1999

[54] METHOD FOR TREATING SEXUAL DYSFUNCTION DISORDERS WITH COMPOSITIONS CONTAINING GINKGO BILOBA

[76] Inventor: Alan J. Cohen, 2340 Ward St. #201, Berkeley, Calif. 94705

[21] Appl. No.: 08/863,175

[22] Filed: May 23, 1997

Related U.S. Application Data

[XX .
[60] Provisional application No. 60/018,226, May 23, 1996.
[51] Int. Cl.$^6$ ..................................................... A61K 35/78
[52] U.S. Cl. ......................................... 424/195.1; 514/922
[58] Field of Search .......................... 424/195.1; 514/922

[56] References Cited

U.S. PATENT DOCUMENTS 4,777,033  10/1988  Ikura et al. ............................... 424/44

OTHER PUBLICATIONS

Treatment of Antidepressant–induced Sexual Dysfunction by Alan J Cohen; Jan. 1996, Heathwatch, vol. 6, #1, p. 3.
Ginkgo Improves Circulation and Brain Function, by Ken Babal Health & Healing, Summer 1995.
Halama, Therapiewoche, 40:3760–3765, 1990.
Balon et al. J. Clin. Psychiatry, 54:209–212, 1993.
Hobbs, Ginkgo–Elixir of Youth, Miovic, ed., Botanic Press, CA, p. 63, 1994.
Rockhold, Drug Dev. Res., 25:85–95, 1992.
Palacios et al., Maturitas, 22:155–161, 1995.
Davidson, Depression, 2:233–240, 1995.
Dictionary of Drugs: Chemical Data, Structures and Bibliographies, p. 857, 1990.
Kleijnen et al., Lancet, 340:1136–1139, 1992.

*Primary Examiner*—Michael G. Wityshyn
*Assistant Examiner*—Janet M. Kerr
*Attorney, Agent, or Firm*—Coudert Brothers

[57] ABSTRACT

A method for treating sexual dysfunction in a patient taking antidepressant medication is described, comprising administering an effective amount of ginkgo biloba to the patient. A method for treating sexual dysfunction in a patient taking anti-hypertensive medication is described, comprising administering an effective amount of ginkgo biloba to the patient. A method for treating sexual dysfunction in menopausal or perimenopausal patients is described, comprising administering an effective amount of ginkgo biloba to the patient. A method for treating sexual dysfunction that is not caused by a medication is described. A method for enhancing sexual response and performance is described. The invention further encompasses an antidepressant composition for the treatment of a patient in need of antidepressant therapy which comprises an amount of antidepressant sufficient to alleviate the depression and an amount of Ginkgo Biloba sufficient to alleviate any sexual dysfunction associated with the antidepressant.

24 Claims, No Drawings

METHOD FOR TREATING SEXUAL DYSFUNCTION DISORDERS WITH COMPOSITIONS CONTAINING GINKGO BILOBA

This application claims benefit of prior U.S. provisional application Ser. No. 60/018,226 filed May 23, 1996, incorporated herein by reference.

I. BACKGROUND OF THE INVENTION

1. Field of the Invention

This invention relates generally to a method and medication for treating sexual dysfunction and more specifically to a treating drug-induced sexual dysfunction.

2. Description of Related Art

Sexual dysfunction is commonly associated with antidepressant drugs (J. R. T. Davidson, *Sexual dysfunction and antidepressants, Depression* 2:233–240 1994,95; Richard Balon, et al., Sexual Dysfunction during antidepressant treatment, J. Clin. Psychiatry Update Monograph, 1:1 November 1994). Patients' complaints relate to decreased libido, erectile dysfunction, orgasmic and ejaculatory problems. Several treatments have been tried to alleviate patients' complaints of sexual dysfunction, but only limited success has been reported (Bartlik, B., Kaplan, P., Kaplan, H. S., *Psychostimulants apparently reverse sexual dysfunction secondary to selective serotonin re-uptake inhibitors*, J. Sex Mar Ther., 21(4):264–271, Winter 1995). Several pharmacological formulations have been used in attempts to intervene in the onset of this unwanted side effect. They include administering amantadine, amphetamine, buspirone, cyproheptadine, ginseng, Ritalin®, and yohimbine. These attempts at pharmaceutical intervention have not been satisfactory.

The antidepressant, fluoxetine, commercially available under the trade designation Prozac®, has been found to reduce sexual reaction so effectively that it is successfully used to treat premature ejaculation (U.S. Pat. No. 5,151,448). However, for patients seeking only the antidepressant effect of fluoxetine, the associated reduction in libido, reduced or delayed orgasm, delayed ejaculation, and erectile dysfunction is significant enough to prevent patients' use of the drug. It would be highly desirable if antidepressant drugs could be administered without the unwanted side affect of sexual dysfunction.

Estimates of the incidence of sexual dysfunction attributed to antidepressant use vary from approximately 2% to over 90%. The antidepressants commonly reported as most likely to cause sexual dysfunction include heterocyclic antidepressants, monamine oxidase inhibitors, selective serotonin reuptake inhibitors, venlafaxine, bupropion, and nefazodone.

Ginkgo Biloba L. (hereinafter referred to as "Ginkgo") has in the past been used to treat asthma and bronchitis. The Chinese have used it for these purposes for centuries and more recently the German pharmaceutical company, Schwabe, has marketed Gingko as a prescription drug for the same purpose. Gingko is a Japanese name used by German surgeon, Kaempfer in 1712. The plant was known as Salisburia adiantifolia Sm. until Linnaeus, a Swedish botanist, gave it the Latin name, Ginkgo biloba L in 1771. The Ginkgo fruit is known by the Chinese as Pak-Ko.

Christopher Hobbs, in a book titled *Ginkgo, Elixir of Youth* (Botanica Press, Box 742, Capitola, Calif. 95010, 1991), provides one of the most complete lists of medical uses for Gingko preparations. He presents over 140 references on medical uses of Gingko preparations. His thorough discussion includes traditional Chinese medical uses and modern western medical uses of Gingko preparations. He discusses use of Gingko preparations to treat allergies, loss of alertness, asthma, vertigo, circulatory problems including cerebral insufficiency, low glucose metabolism in the brain, depression, hearing loss, ringing in the ears, heart disease, mental confusion, intellectual weakness, stroke, retina damage, and memory loss. While most traditional Chinese preparations focused on use of the Ginkgo nut, or fruit, most modern preparations are made from the Ginkgo leaves.

A 1992 medical review (Jos Kleijnen and Paul Knipschild, Lancet, v.340, Nov. 7, 1992 cited the main indications for ginkgo as peripheral vascular disease such as intermittent claudication and cerebral insufficiency, where the latter comprised mental confusion, anxiety, dizziness, headache, and other symptoms associated with impaired cerebral circulation. In another study, Ginkgo biloba was found to act as a smooth muscle relaxant. Puglisi et al. (Pharm Res Comm, 20(7): 573, 1988) studied the therapeutic potential of flavonoids from Ginkgo biloba L. in the treatment of respiratory distress found the flavonoids acted on tracheal smooth muscle cells. There has been no evidence that Ginkgo Biloba L. has utility other than for respiratory or vasoregulatory and circulatory complaints.

The Merck Index, 11th ed., Susan Budacari, Ed., (Merck & Co., Rahway N.J., 1989), pg. 693, lists Ginkgo Biloba extract as a defined extract obtained from the leaves of Ginkgo biloba L., also known as Salisburia adiantifolia Smith. Several cites for its preparation are given. Its therapeutic category is "In cerebral and peripheral circulatory disturbances".

All antidepressants are associated with some likelihood of inducing sexual dysfunction. The consequences of sexual dysfunction induced by antidepressants is significant and can result in patients not complying with treatment, leading in turn to relapse in depression and subsequent morbidity and mortality. It clearly would be highly desirable and beneficial to users of antidepressant medication if there were a medication that would alleviate this adverse side-effect of antidepressant medication.

II. SUMMARY OF THE INVENTION

The present invention comprises a method for treating sexual dysfunction in men and women comprising administering an effective amount of Ginkgo to the patient.

It is an object of this invention to provide a medication and method of treatment that alleviates the sexual dysfunction side-affect associated with taking some medications. The invention provides a method for treating sexual dysfunction in a patient taking a medication that has sexual dysfunction as a side-affect, such as antidepressants and antihypertensives, comprising administering an effective amount of Ginkgo Biloba L. (hereinafter referred to as "Gingko") to the patient.

The present invention further encompasses an antidepressant composition for the treatment of a patient in need of antidepressant therapy which comprises an amount of antidepressant sufficient to alleviate the depression and an amount of Ginkgo sufficient to alleviate any sexual dysfunction associated with the antidepressant.

Additionally, the invention provides a method for generally enhancing sexual function and relieving sexual dysfunction for people who are not taking medications that have sexual dysfunction as a side-affect.

III. DETAILED DESCRIPTION OF THE INVENTION

The present invention comprises a method for treating sexual dysfunction in men and women comprising administering an effective amount of Ginkgo to the patient. Additionally, the present invention provides a medication and method of treatment that alleviates the sexual dysfunction side-affect associated with taking some medications.

The present invention further provides a method to reverse or reduce sexual dysfunction related to antidepressant medication comprising administration of an effective amount of Gingko plant material to a patient taking antidepressant drugs.

The present invention yet further provides a method to reverse or reduce sexual dysfunction related to antihypertensive medication comprising administration of an effective amount of Gingko plant material to a patient taking antihypertensive drugs.

Additionally, the present invention provides a method to enhance sexual function for people who are not taking medication having sexual dysfunction as a side-affect, but who are experiencing sexual dysfunction, comprising administration of an effective amount of Gingko plant material.

As used herein, the term "sexual dysfunction" means a medical diagnosis according to the Diagnostic and Statistical Manual of Mental Disorders, 4th edition, (DSM-IV), Washington DC, American Psychiatric Association, 1996 and includes the criteria, types, disorders, and subtypes of sexual dysfunction listed therein.

As used herein, the term "standardized Ginkgo extract" means a 50:1 concentration made from the Ginkgo Biloba leaf and containing between about 24% and about 25% ginkgo-flavone-glycosides. When a dose of 60 milligrams Ginkgo (60 mg. Ginkgo), is cited, it refers to 60 mg. of standardized Gingko extract preparation. The notation, "2, 60 mg, 2×/day", means 2 60 mg. tablets or capsules of standardized Gingko extract taken twice a day for a total of 4 capsules or tablets per day (240 mg. Ginkgo per day).

Gingko can be administered using a variety of preparations. Teas and food products can be made from the Ginkgo nut; the leaves can also be brewed into tea. Most modern preparations use extracts made from Ginkgo leaves. Some methods of preparation are discussed in Christopher Hobbs' book (op. cit.) and in an article by Ken Babal, *Ginkgo Improves Circulation and Brain Function*, Health and Healing, Summer 1995, pg. 9, reprinted from "Health Store News". Babal states that, "A consistent pharmacological action can be expected when a 50:1 concentration made from the leaf is standardized to contain 24% ginkgo-flavone-glycosides and 6% terpene lactones." The Hobbs and Babal citations are not typical references used by the medical community. In a more conventional medical reference, Jos Kleinjnen and Paul Knipschild (Lancet, v 340, pg. 1136, Ginkgo biloba) describe making extracts from dried leaves, using a multistep procedure. ". . . the liquid extract is dried to give 1 part extract from 50 parts raw drug (leaves)." They use four different ginkgo preparations in the trials they discuss, Tebonin®, Tanakan®, Rökan®, and Kaveri®. The first three are standardized to 24% ginkgo-flavone glycosides and 6% terpenoids (a compound denoted as EGb761). Kaveri® uses 25% ginkgo-flavone glycosides and 6% terpenoids (a compound denoted as LI 1370). The ginkgo-flavone glycosides are sometimes referred to as heterosides. The advantage of standardizing preparation and concentration of some active ingredients is to facilitate comparison studies. Clearly, the particular values chosen are somewhat arbitrary and other efficacious preparations using different concentrations would work.

Hobbs also describes preparation of Gingko in a liquid extract, or tincture. The tincture is prepared by soaking fresh, or dried and possibly powdered, leaves in alcohol and water for two weeks or more. Powdered extracts (cited by Hobbs as concentrated to 6:1 or 8:1) or simple powdered leaves in capsule or tablet form can also be administered.

Therapeutic doses can be as low as about 20 mg Ginkgo per day. Even high doses of ginkgo extract do not appear to cause side effects (Fleber, J. P. 1988 *Effect of Ginkgo biloba extract on the endocrine parameters*, In Funfgeld, Rokan®; Schwabe, W. Arzneimittel [d.m.] Tebonin forte® (detail manual); Schilcher, H. Ginkgo biloba: investigation on the quality, activity, effectiveness, and safety, Zeit. F. Phytother. 9:119–127, 1988). At very large doses, some patients experience stomach upset that is reversible by decreasing the dose. The dose may range as high as 5 grams per day or more, although the present inventor has observed remission of sexual dysfunction at much lower doses. More preferably, the daily dose administered is between about 40 mg. and about 2 gm. Ginkgo per day. Even more preferably, a dose between about 80 mg and about 1 gm Ginkgo per day was shown therapeutically efficacious. Many patients had full remission of sexual dysfunction using doses between about 100 mg and about 600 mg. Ginkgo per day. For most patients, administration of between about 120 mg and about 240 mg. Ginkgo per day was effective in reversing antidepressant induced sexual dysfunction.

The standard preparation used above is quite arbitrary. It's consistency aids in making comparisons. If a different preparation was used, that resulted in different concentrations of the active Ginkgo ingredients per mg of medication, the dose of that preparation would be adjusted accordingly. Making these adjustments is obvious to the ordinary practitioner in pharmacology or medicine.

The medical diagnosis of sexual dysfunction is clearly described in the Diagnostic and Statistical Manual of Mental Disorders, 4th edition, (DSM-IV), Washington DC, American Psychiatric Association, 1996 (incorporated herein by reference). It includes, sexual desire disorders such as hypoactive sexual desire disorder and sexual aversion disorder; sexual arousal disorders such as female sexual arousal disorder and male erectile disorder; orgasmic disorders such as female orgasmic disorder (formerly, inhibited female orgasm), male orgasmic disorder (formerly, inhibited male orgasm), and premature ejaculation. Additionally included in the DSM-IV are several subtypes that apply to primary sexual dysfunctions. The subtypes are, lifelong type, acquired type, generalized type, situational type, and sexual dysfunction due to psychological factors or due to combined factors. Sexual dysfunction due to general medical condition and substance-induced sexual dysfunction are also included in the DSM-IV.

The present invention comprises a method for treating sexual dysfunction in men and women comprising administering an effective amount of Ginkgo to the patient.

Fifty-five patients were enrolled in an open trial using formulations of standardized ginkgo extract generally commercially available. All patients had previously attempted to reduce or eliminate sexual dysfunction related to their antidepressant regimen. The previous attempts included administration of cyproheptadine, yohimbine, amatandine, buspirone, or adjusting the dose of antidepressant. None of these methods provided satisfactory relief from the sexual dysfunction. The participating patients agreed to use ginkgo biloba for treatment of sexual dysfunction secondary to their antidepressant medication. All patients met the Diagnostic and Statistical Manual IV (DSM IV) criteria for a depressive disorder. Subtypes include Major Depression, Recurrent, Nonpsychotic, Schizoaffective Disorder, Depressed Type, Cyclothymia, and Major Depression Single Episode. Medications administered included selective serotonin reuptake inhibitors, venlafaxine, nefazodone and bupropion. Patients were prescribed a formulation of standardized Ginkgo extract containing 24% heterosides, in 40 mg. or 60 mg. capsules, to be taken three to four times per day as tolerated (Alan Cohen, Treatment of Antidepressant-induced Sexual Dysfunction, Healthwatch, 6(1): Jan 3, 1996). For most patients the dose administered was between about 120 mg. and about 240 mg. per day. After a four week trial period, they were reevaluated for symptoms of sexual dysfunction. The symptoms had included anorgasmia, decreased libido, difficulty with erection, or delayed ejaculation. Forty-nine of the 55 patients reported significant response and improvement in their sexual dysfunction. There were no significant adverse effects associated with use of the Ginkgo, except for one patient who reported worsening of urinary difficulties related to prostatic hypertrophy.

For most patients, administration of between about 120 mg. and about 240 mg. Ginkgo per day was effective in reversing antidepressant induced sexual dysfunction.

Standardized Ginkgo extract from any of a variety of common distribution sources is useful in the relief of sexual dysfunction induced by antidepressant medication. Patients variously obtained their medications from local health food stores, mail order houses, and other sources. One source commonly used by patients in the studies described above is The Vitamin Shoppe, located in N. Bergen, N.J. 07047, telephone, 1 800 223-1216. Another source is CFIDS Buyers Health Club, telephone, 1 800 366-6056. Yet a third source used by patients in the current study is the General Nutrition Center (GNC) chain of health food stores.

For the treatment contemplated by the present invention, oral administration is preferred. However, other routes of administration can also be used, such as peritoneal, by suppositories, skin patch, liquid tincture, injection, and the like. Oral administration can be in the form of a tablet, capsule, liquid, or food additive.

The specific dosage and duration of treatment may vary depending upon the particular patient. In the studies described above, relief from antidepressant induced sexual dysfunction was obtained by administering Ginkgo biloba three or four times a day in tablet or capsule form. Some patients divided the dose into only two ingestions per day, primarily for convenience, with no loss in effect. In some cases a larger single dose per day may be ingested, or a smaller dose may be ingested three or more times per day depending on the schedule and inclination of the patient. Each ingestion may range from about 20 mg. to about 1000 mg. More preferably, primarily for convenience, each ingestion is between about 30 mg and about 800 mg. Alternatively, each ingestion is between 40 mg and 600 mg.

The total amount of Ginkgo Biloba administered per day is a critical parameter. Independent of the number of times the patient ingests a dose of the compound, the total dose per day is preferably in the range between about 20 mg and about 5 grams. More practically, a daily dose in the range of about 40 mg to about 2 gm is administered. In the studies above, satisfactory relief from antidepressant-induced sexual dysfunction was obtained from a daily dosage between about 80 mg (1 80 mg. capsule, 1×/day) to about 240 mg (2 60 mg. capsules, 2×/day).

A majority of patients prefer taking the medication in two ingestions per day. The benefits of the Ginkgo typically take between 3 days and about 1 month to manifest.

The present invention further encompasses an antidepressant composition for the treatment of a patient in need of antidepressant therapy. The novel composition comprises an amount of antidepressant sufficient to alleviate the depression and an amount of Ginkgo sufficient to alleviate any sexual dysfunction associated with the antidepressant. Standard methods of preparation for pharmaceutical formulations are used and the amount of antidepressant and Ginkgo contained in each preparation can be varied according to the standard doses likely to be prescribed.

One convenient form for administering the inventive combination is in the form of tablets or capsules to be taken orally. A formulation using a therapeutic combination of compounds is formulated comprising antidepressant and Ginkgo wherein the combination of active ingredients is present in an effective amount (hereinafter referred to as "therapeutic combination"). Examples of antidepressants that are beneficially combined with Ginkgo in order to ameliorate symptoms of sexual dysfunction include, but are not limited to bupropion, venlafaxine, fluoxetine, nefazodone, sertraline, phenelzine, paroxetine, and trazodone. Optionally the therapeutic combination further includes at least one pharmaceutically acceptable carrier. Examples of some inventive therapeutic combinations comprising antidepressants combined with Gingko that meet some frequently prescribed treatment regimens are listed below.

Therapeutic combination 1: a therapeutic combination containing about 40 mg fluoxetine and about 250 mg Ginkgo, to be administered once a day.

Therapeutic combination 2: a therapeutic combination containing about 20 mg fluoxetine and about 120 mg Ginkgo, to be administered twice a day.

Therapeutic combination 3: a therapeutic combination containing about 10 mg fluoxetine and about 120 mg Ginkgo, to be administered twice a day.

Therapeutic combination 4: a therapeutic combination containing about 10 mg venlafaxine and about 250 mg Ginkgo, to be administered once a day.

Therapeutic combination 5: a therapeutic combination containing about 25 mg venlafaxine and about 120 mg Ginkgo, to be administered three times a day.

In the inventive therapeutic combination, the Ginkgo may be dispensed in a time release form. As will be easily apparent to the ordinary practitioner, the above therapeutic combinations may be in the form of tablets or capsules and the novel combination of antidepressant and Ginkgo may be further augmented with Gingko tablets or capsules that do not contain antidepressant medication.

The following examples further illustrate the present invention. They are not intended to limit the scope of the invention. Various modifications, alternative constructions and equivalents may be employed without departing from the true spirit and scope of the invention.

EXAMPLE 1

A 48 year old married male with Major Depression, first episode, found good relief of his depressive symptoms when administered 40 mg./day of Prozac®. However, he developed loss of libido and erectile failure. His Prozac® dose was reduced in an unsuccessful attempt to reverse the sexual dysfunction. Yohimbine was administered in an attempt to provide a pharmaceutical intervention but resulted in anxiety without improvement of the patient's sexual dysfunction. The Yohimbine was discontinued. Ginkgo Biloba (50:1 concentration, obtained from CFIDS Health Buyers Club) standardized to contain 24% ginkgo flavone glycosides and 6% terpene lactones was administered by having the patient take two 60 mg capsules twice a day, totaling 240 mg taken per day. Ten days after the patient began supplementing his normal 40 mg./day regimen of Prozace with the above regimen of Gingko Biloba, he experienced complete remission of all sexual dysfunction with no loss in efficacy of the antidepressive medication.

EXAMPLE 2

A 45 year old married female with pain, anxiety, and depression found good relief of symptoms by taking 20 mg Prozac® once a day and 1 mg lorazepam (generic for Adavan® or Valium®) twice a day. She developed sexual dysfunction in the form of reduced libido and anorgasmia. Pharmaceutical intervention was attempted, unsuccessfully, by adding Amatadine to her regimen. The Amatadine was discontinued. Ginkgo Biloba (obtained from the Vitamin Shoppe) containing 24% Gingko heteroside, was added to the patient's regimen at a dose of two 60 mg. capsules taken twice a day. After two weeks on this regimen the patient experienced return of normal sexual response with continued good control of her mood disorder symptoms.

EXAMPLE 3

A 41 year old married female with single a episode of Major Depression responded well to 50 mg. selective seritonin reuptake inhibitor, sertraline (generic for Zoloft®) administered once per day. She developed delayed orgasm and reduced libido. When the amount of Zoloft® taken was reduced in order to address the side effect of sexual dysfunction, the depressive symptoms reappeared. She returned to her original regimen of Zoloft® and added Ginkgo Biloba, concentrated 50:1, taking two 60 mg capsules twice a day, totaling 240 mg per day. The Gingko was obtained from GNC. In two weeks, she experienced relief from all symptoms of sexual dysfunction.

EXAMPLE 4

A 45 year old married female responded well to 50 mg per day sertraline. However, she experienced decreased libido and trouble reaching orgasm. In response to her complaints regarding sexual dysfunction, Ginkgo was administered in capsule form at a dose of 40 mg taken once per day. She reported relief from symptoms of sexual dysfunction after two weeks.

EXAMPLE 5

A 31 year old male, suffering from organic depression found relief when he began taking 60 mg per day fluoxetine. However, he developed a frustrating decrease in libido. Symptoms of reduced libido were reversed by taking 600 mg Ginkgo once a day.

EXAMPLE 6

Table I below shows summary results from a study in which Gingko Biloba was administered to patients with complaints of sexual dysfunction related to administration of antidepressant medication. Forty-nine of the fifty-five patients reported significant response and improvement in their sexual dysfunction.

TABLE I

| Patient # | Gender | Antidepressant medication | Sexual dysfunction Symptoms | Ginkgo Dose per day | Relief |
|---|---|---|---|---|---|
| 1 | M | bupropion | reduced libido | 240 mg | yes |
| 2 | F | venlafaxine | anorgasmic reduced libido | 240 mg | yes |
| 3 | F | fluoxetine | anorgasmic reduced libido | 180 mg | yes |
| 4 | F | fluoxetine | anorgasmic reduced libido | 240 mg | yes |
| 5 | M | bupropion | reduced libido | 120 mg | yes |
| 6 | M | nefazodone | reduced libido | 240 mg | yes |
| 7 | M | fluoxetine | reduced libido | 240 mg | yes |
| 8 | M | sertraline | erectile failure | 240 mg | yes |
| 9 | M | sertraline | reduced libido erectile failure | 120 mg | yes |
| 10 | M | nefazodone | anorgasmic erectile failure | 240 mg | yes |
| 11 | M | bupropion | erectile failure reduced libido | 180 mg | yes |
| 12 | M | bupropion | erectile failure reduced libido | 120 mg | yes |
| 13 | F | fluoxetine | anorgasmic reduced libido | 240 mg | yes |
| 14 | M | bupropion | reduced libido | 240 mg | no |
| 15 | F | fluoxetine | anorgasmic reduced libido | 240 mg | yes |
| 16 | F | phenelzine | anorgasmic reduced libido | 240 mg | yes |
| 17 | M | bupropion | erectile failure reduced libido | 240 mg | yes |
| 18 | F | venlafaxine | anorgasmic reduced libido | 240 mg | no |
| 19 | M | sertraline | reduced libido | 120 mg | yes |
| 20 | M | fluoxetine | erectile failure anorgasmic reduced libido | 240 mg | yes |
| 21 | M | bupropion | reduced libido anorgasmic | 240 mg | no |
| 22 | M | venlafaxine | reduced libido erectile failure | 180 mg | no |
| 23 | F | fluoxetine | reduced libido anorgasmic | 180 mg | yes |
| 24 | M | paroxetine | reduced libido | 120 mg | yes |
| 25 | F | venlafaxine | anorgasmic reduced libido | 180 mg | yes |
| 26 | M | sertraline | reduced libido | 120 mg | yes |
| 27 | F | fluoxetine | reduced libido anorgasmic | 120 mg | yes |
| 28 | F | sertraline | reduced libido anorgasmic | 180 mg | yes |
| 29 | F | venlafaxine | reduced libido anorgasmic | 120 mg | yes |
| 30 | M | fluoxetine | reduced libido erectile failure | 240 mg | yes |
| 31 | F | fluoxetine | reduced libido | 120 mg | yes |
| 32 | F | fluoxetine | anorgasmic reduced libido | 120 mg | yes |
| 33 | M | paroxetine | erectile failure reduced libido | 240 mg | yes |
| 34 | F | fluoxetine | anorgasmic reduced libido | 240 mg | yes |
| 35 | M | bupropion | reduced libido erectile failure | 120 mg | yes |
| 36 | M | bupropion | reduced libido | 180 mg | yes |
| 37 | F | venlafaxine | reduced libido anorgasmic | 240 mg | yes |
| 38 | M | fluoxetine | reduced libido anorgasmic | 180 mg | yes |
| 39 | M | fluoxetine | reduced libido erectile failure | 240 mg | no |
| 40 | F | venlafaxine | anorgasmic reduced libido | 240 mg | yes |
| 41 | M | paroxetine | reduced libido erectile failure | 240 mg | yes |

TABLE I-continued

| Patient # | Gender | Antidepressant medication | Sexual dysfunction Symptoms | Ginkgo Dose per day | Relief |
|---|---|---|---|---|---|
| 42 | F | fluoxetine | reduced libido anorgasmic | 240 mg | yes |
| 43 | F | sertraline | reduced libido anorgasmic | 240 mg | yes |
| 44 | F | fluoxetine | anorgasmic reduced libido | 180 mg | yes |
| 45 | M | venlafaxine | reduced libido erectile failure | 300 mg | no |
| 46 | F | paroxetine | anorgasmic reduced libido | 240 mg | yes |
| 47 | F | sertraline | anorgasmic reduced libido | 240 mg | yes |
| 48 | F | fluoxetine | anorgasmic reduced libido | 120 mg | yes |
| 49 | M | fluoxetine | reduced libido | 240 mg | yes |
| 50 | M | fluoxetine | reduced libido erectile failure | 240 mg | yes |
| 51 | M | fluoxetine | reduced libido anorgasmic | 240 mg | yes |
| 52 | F | sertraline | anorgasmic reduced libido | 180 mg | yes |
| 53 | F | trazodone | reduced libido anorgasmic | 240 mg | yes |
| 54 | M | fluoxetine | reduced libido | 180 mg | yes |

The data from the study summarized in Table I shows 49 out of 54 patients, that is 92%, experiencing relief from drug-induced sexual dysfunction upon taking between about 120 mg and about 240 mg standardized Ginkgo extract.

In other situations, the inventor has observed as little as 40 mg per day of standardized ginkgo extract to provide relief from symptoms of sexual dysfunction. Even smaller amounts typically provide the sought-after relief for those with lower body mass than the patients who benefited from 40 mg per day. Additionally, patients taking as much as 1 gram per day of standardized ginkgo extract experienced no undesirable side effects.

EXAMPLE 7

A male taking a standard prescription of anti-hypertensive medication, prinivil, experienced chronic male erectile disorder including reduced libido and erectile failure. A regimen of 2, 60 mg, 2×/day brought relief of both symptoms.

EXAMPLE 8

A 45 year old female who was not taking antidepressant or anti-hypertensive medication complained of reduced libido. The patient took two 60 mg capsules Ginkgo twice a day, totaling 240 mg per day and experienced relief of symptoms in about 10 days.

EXAMPLE 9

Approximately 3 females and 3 males, between the ages of 25 and 60, who were not taking either antidepressant or anti-hypertensive medication and who were not suffering from sexual dysfunction, reported heightened sexual response and enhanced sexual performance upon taking doses of Ginkgo between about 40 mg per day and about 1 gm per day.

EXAMPLE 10

A 51 year old perimenopausal woman who was not taking either antidepressant or anti-hypertensive medication reported enhanced sexual response including stronger libido and enriched orgasm upon taking between about 120 mg per day and about 240 mg per day. When she neglected to take the Ginkgo, her libido returned to the slightly subdued level she attributed to age. Enhanced sexual enjoyment was restored when she remembered to take Ginkgo.

EXAMPLE 11

A 55 year old menopausal woman who was not taking either antidepressant or anti-hypertensive medication reported enhanced sexual response including increased libido and relief from anorgasmic symptoms when she took about 180 mg per day for 3 weeks.

EXAMPLE 12

Each partner of a married couple suffered from low libido. The 40 year old woman was not taking antidepressant medication. After taking 60 mg twice per day for two months, she experienced significantly enhanced libido. Her spouse, a 41 year old male, was on a standard Effexor regimen to treat depression. He also suffered from low libido. After adding a Ginkgo regimen of 60 mg, twice per day for two months, he also experienced significant enhancement of libido. The couple reported greatly enhanced sexual experience together, improving an important aspect of their married life.

Thus, the invention provides a method for alleviating sexual dysfunction associated with administration of many antidepressant medications.

The invention further provides a method for alleviating sexual dysfunction associated with administration of anti-hypertensive medication.

The invention further provides a method for alleviating sexual dysfunction associated with menopause.

The invention further provides a method for enhancing sexual performance of males and females who are not suffering from sexual dysfunction.

The description of illustrative embodiments and best modes of the present invention is not intended to limit the scope of the invention. Various modifications, alternative constructions and equivalents may be employed without departing from the true spirit and scope of the appended claims.

Having thus described the invention, what is claimed is:

1. A method for treating sexual dysfinction disorders in a patient wherein the disorders are selected from the group consisting of hypoactive sexual desire disorder, sexual aversion disorder, orgasmic disorder, and female sexual arousal disorder, comprising administering an effective amount of Ginkgo to treat the sexual dysfunction disorder in the patient.

2. The method of claim 1 wherein Ginkgo is administered daily in an amount between about 20 milligrams and about 2 grams.

3. The method of claim 1 wherein at least 40 mg Ginkgo is administered daily.

4. The method of claim 1 wherein Ginkgo is administered daily in an amount between about 50 milligrams and about 1 gram.

5. The method of claim 1 wherein Ginkgo is administered daily in an amount between about 120 milligrams and about 240 milligrams.

6. The method of claim 1 wherein Ginkgo is administered orally between one time daily and five times daily to the patient.

7. The method of claim 1 wherein Ginkgo is administered orally between two times daily and four times daily to the patient.

8. A method for treating a patient experiencing sexual dysfunction disorders associated with administration of antidepressant medication, wherein the disorders are selected from the group consisting of hypoactive sexual desire disorder, sexual aversion disorder, orgasmic disorder, and female sexual arousal disorder, comprising administering an effective amount of Ginkgo to treat the sexual dysfuction disorders in the patient.

9. The method of claim 8 wherein Ginkgo is administered daily in an amount between about 20 milligrams and about 2 grams.

10. The method of claim 8 wherein at least 40 mg Ginkgo is administered daily.

11. The method of claim 8 wherein Ginkgo is administered daily in an amount between about 50 milligrams and about 1 gram.

12. The method of claim 8 wherein Ginkgo is administered daily in an amount between about 120 milligrams and about 240 milligrams.

13. The method of claim 8 wherein Ginkgo is administered orally between one time daily and five times daily to the patient.

14. The method of claim 8 wherein Ginkgo is administered orally between two times daily and four times daily to the patient.

15. A method for treating a patient experiencing sexual dysfunction disorders associated with administration of antihypertensive medication, wherein the disorders are selected from the group consisting hypoactive sexual desire disorder, sexaul aversion disorder, orgasmic disorder, and female sexual arousal disorder, comprising administering an effective amount of Ginkgo to treat the sexual dysfunction disorders in the patient.

16. The method of claim 15 wherein Ginkgo is administered daily in an amount between about 20 milligrams and about 2 grams.

17. The method of claim 15 wherein at least 40 mg Ginkgo is administered daily.

18. The method of claim 15 wherein Ginkgo is administered daily in an amount between about 50 milligrams and about 1 gram.

19. The method of claim 15 wherein Ginkgo is administered daily in an amount between about 120 milligrams and about 240 milligrams.

20. The method of claim 15 wherein Ginkgo is administered orally between one time daily and five times daily to the patient.

21. The method of claim 15 wherein Ginkgo is administered orally between two times daily and four times daily to the patient.

22. A method for treating a patient experiencing sexual dysfunction disorders associated with menopause wherein the disorders are selected from the group consisting of hypoactive sexual desire disorder, sexual avsersion disorder, orgasmic disorder, and female sexual arousal disorder comprising administering an effective amount of Ginkgo to treat the sexual dysfunction disorders in the patient.

23. The method of claim 22 wherein Ginkgo is administered daily in an amount between about 20 milligrams and about 2 grams.

24. The method of claim 22 wherein at least 40 mg Ginkgo is administered daily.

* * * * *

UNITED STATES PATENT AND TRADEMARK OFFICE
CERTIFICATE OF CORRECTION

PATENT NO. : 5,897,864
DATED : April 27, 1999
INVENTOR(S) : Alan J. Cohen

It is certified that error appears in the above-indentified patent and that said Letters Patent is hereby corrected as shown below:

| Col. | Line | |
|------|------|---|
| 2 | 14 | After "11/7/92" insert --)--. |
| 3 | 56 | Delete "Ginkgo biloba" and insert therefor --*Ginkgo biloba*--. |
| 4 | 16, 17 | Delete "Ginkgo biloba investigation on the quality activity, effectiveness and safety" and insert therefor --*Ginkgo biloba investigation on the quality activity, effectiveness and safety*--. |
| 5 | 14 | Delete "Healthwatch" and insert therefor --*Healthwatch*--. |
| 7 | 11 | Delete "Prozace" and insert therefor --Prozac®--. |

Signed and Sealed this

Twenty-third Day of January, 2001

Attest:

Q. TODD DICKINSON

*Attesting Officer*       *Commissioner of Patents and Trademarks*

UNITED STATES PATENT AND TRADEMARK OFFICE
CERTIFICATE OF CORRECTION

PATENT NO. : 5,897,864
DATED : April 27, 1999
INVENTOR(S) : Alan J. Cohen

It is certified that error appears in the above-identified patent and that said Letters Patent is hereby corrected as shown below:

Title page,
Item [76], please inventor's address to the following:
6571 Liggett Drive, Oakland, CA 94611

Signed and Sealed this

Twenty-third Day of October, 2001

Attest:

NICHOLAS P. GODICI
*Attesting Officer*  *Acting Director of the United States Patent and Trademark Office*